United States Patent [19]

Lawford

[11] Patent Number: 4,812,410

[45] Date of Patent: Mar. 14, 1989

[54] CONTINUOUS PROCESS FOR ETHANOL PRODUCTION BY BACTERIAL FERMENTATION

[75] Inventor: Hugh G. Lawford, Mississauga, Canada

[73] Assignee: George Weston Limited, Toronto, Canada

[21] Appl. No.: 735,913

[22] Filed: May 20, 1985

Related U.S. Application Data

[63] Continuation of Ser. No. 722,492, Apr. 12, 1985.

[51] Int. Cl.$^4$ .......................... C12P 7/06; C12N 1/20; C12N 1/38
[52] U.S. Cl. .................................... 435/161; 435/244; 435/813
[58] Field of Search ............... 435/161, 244, 253, 822, 435/813

[56] References Cited

U.S. PATENT DOCUMENTS

| | | | |
|---|---|---|---|
| 2,822,319 | 2/1958 | Monod | 435/813 |
| 4,064,015 | 12/1977 | Nyiri et al. | 195/108 |
| 4,127,447 | 4/1978 | Griffith et al. | 435/161 |
| 4,292,406 | 9/1981 | Ljungdahl et al. | 435/42 |
| 4,333,053 | 2/1981 | Hughes et al. | 435/141 |
| 4,393,136 | 7/1983 | Cheetham | 435/161 |
| 4,403,034 | 9/1983 | Rogers et al. | 435/161 |
| 4,407,954 | 10/1983 | Clyde | 435/161 |
| 4,429,044 | 1/1984 | Boguslawski et al. | 435/220 |
| 4,443,543 | 4/1984 | Rogers et al. | 435/161 |

FOREIGN PATENT DOCUMENTS

0047641 3/1982 European Pat. Off. .
2081305 2/1982 United Kingdom .

OTHER PUBLICATIONS

Rogers et al., *Advances in Biochemical Engineering*, vol. 23 (1983), pp. 37-84.
Biotechnology and Bioengineering, vol. XXIV, 1982, pp. 691-701, John Wiley & Sons Inc., N.Y., US; Kosaric et al., "Fuel Alcohol Biosynthesis by Zymomonas anaerobia: Optimization Studies", p. 691, summary; p. 692, 1, p. 693, 1, p. 698, table 1.
Biotechnology and Bioengineering, vol. 26, no. 4, Apr. 1984, pp. 301-307, John Wiley & Sons Inc., N.Y., US; Wumpelmann et al.; "Ethanol Production with Saccharomyces cerevisiae Under Aerobic Conditions at Different Potassium Concentrations", p. 301, summary.
Chemical Abstracts, vol. 97, no. 1, 5th Jul. 1982, abstract no. 4631g, Columbus, Ohio, US; S. Cromie et al.: "Limitations in Substrate Utilization Efficiency by Zymomonas mobilis", & Eur. J. Appl. Microbiol. Biotechnol. 1982, 14(2), 69-73, Abstract.
J. Swings and J. De Ley, "The Biology of Zymomonas", Bacteriological Reviews, Mar. 1977, pp. 1-46.
J. Bacterial 94, No. 5, 1459-1463 (Nov. 1977).
Adv. Microbiol. Physiol. 5, 213-274 (1971).
Biotechnol. Lett. 3, No. 6, 291-296 (1981).
European J. Appl. Microbiol. Biotechnol. 11, 116-119 (1981).
European J. Appl. Microbiol. Biotechnol. 14, 69-73 (1982).
Appl. and Environ. Microbiol. 44, No. 2, 496-498 (1982).
Appl. Microbiol. Biotechnol. 19, 237-240 (1984).
Appl. and Environ. Microbiol. 48, No. 3, 639-646 (1984).

*Primary Examiner*—Charles F. Warren
*Assistant Examiner*—Irene Marx
*Attorney, Agent, or Firm*—Finnegan, Henderson, Farabow, Garrett & Dunner

[57] ABSTRACT

A continuous process for the production of ethanol by fermentation with strains of Zymomonas is provided. Metabolic processes are limited by the nutrients nitrogen, potassium and phosphorus. When growth is limited by one of these nutrients, the biomass expresses its maximum value for both $q_s$ and $q_p$ at any given value of D and $S_r$. The process is conducted at a lower biomass concentration and a higher specific rate of ethanol formation than a similar process conducted with a nutrient medium that is not limited in nitrogen, potassium or phosphorus. A method of improving performance of Zymomonas in continuous ethanol fermentation at increased temperatures is also provided.

18 Claims, 1 Drawing Sheet

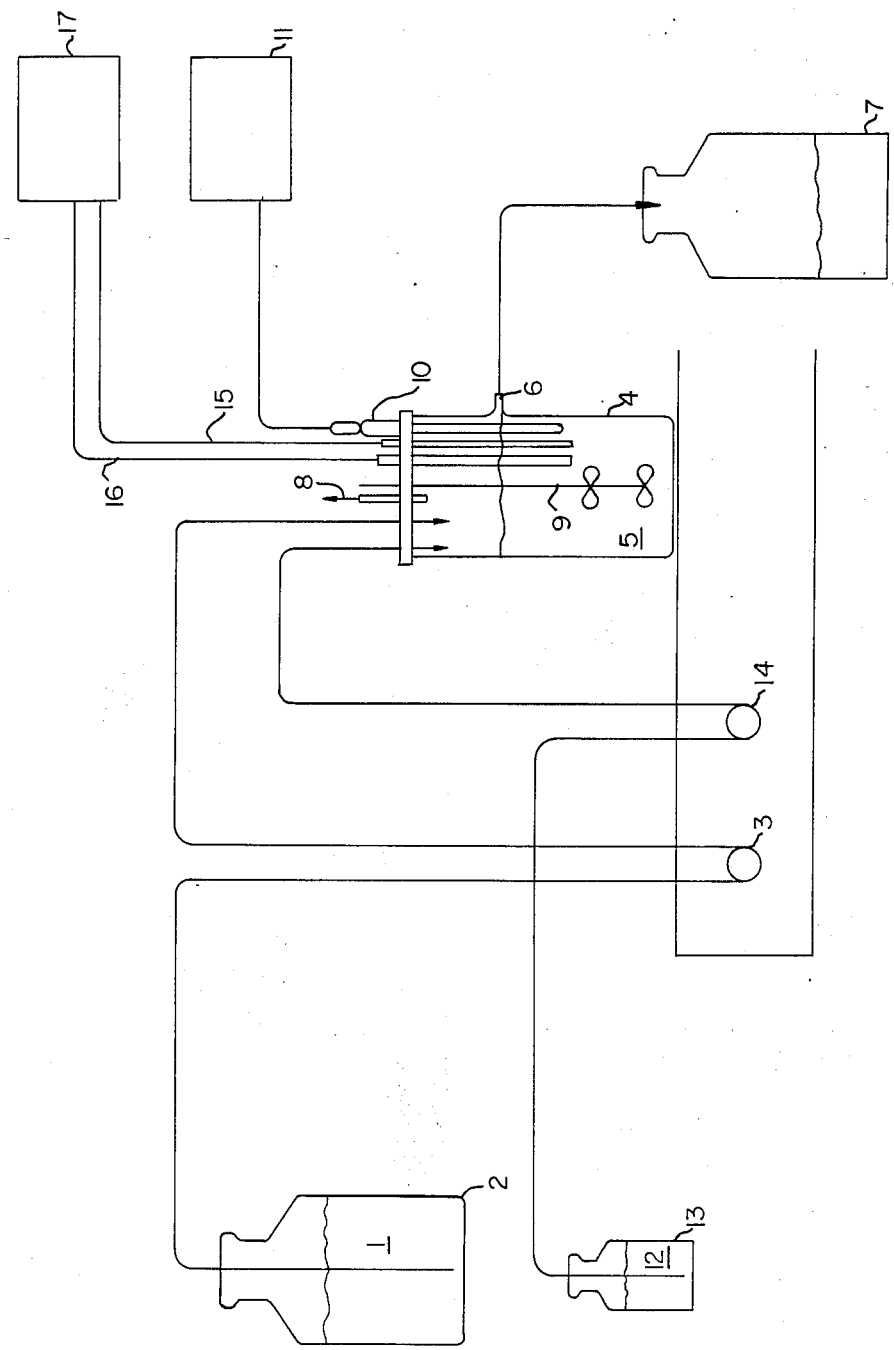

CONTINUOUS PROCESS FOR ETHANOL PRODUCTION BY BACTERIAL FERMENTATION

CROSS-REFERENCE TO RELATED APPLICATION

This application is a continuation of application Ser. No. 722,492, filed Apr. 12, 1985, entitled CONTINUOUS PROCESS FOR ETHANOL PRODUCTION BY BACTERIAL FERMENTATION, the entire contents of which are relied upon and incorporated by reference herein.

BACKGROUND OF THE INVENTION

This invention relates to the bioconversion of a substrate by bacterial fermentation, and more particularly, to a continuous process for the production of ethanol by fermentation using strains of Zymomonas bacteria.

Bacterial ethanol fermentation has been known in the art for many years, and in recent years fermentation using strains of Zymomonas mobilis has received increasing attention. The Z. mobilis strains convert a suitable substrate, such as glucose or another sugar, to ethanol. Significantly higher specific rates of sugar uptake and ethanol production and improved yield compared to traditional yeast fermentation have been reported for these Zymomonas strains.

Fermentation by Z. mobilis has been carried out in batch and continuous culture. The fermentation product (ethanol) is dissolved in the liquid medium in the fermenter. The liquid medium is separated from solids (chiefly biomass) before the ethanol is recovered. Separation of these two phases early in the product-recovery process train is required. Before such a fermentation achieves commercial acceptance, however, productivity must be improved. The reported efforts to date have focused on developing more productive bacterial strains and modifying the configuration of the fermenter used in the fermentation. For example, improvement in ethanol productivity using a continuous culture with a cell recycle system has been reported with Z. mobilis strains.

Recovery of the fermentation product can be a complex and multifaceted task. A significant proportion of the overall cost in a fermentation plant often must be spent for ethanol recovery. A recently reported technique involves the use of a flocculent strain of Z. mobilis that settles in the fermenter allowing the supernatant containing the ethanol to be withdrawn while leaving a majority of the cells in the fermenter. This method is based on the well-known gravity sedimentation principle for separating liquids and solids. The more conventional approaches for separating fermentation broth from biomass involve the withdrawal of a portion of the culture medium from the fermenter and separation of the two phases by centrifugation or filtration techniques. Regardless of the technique employed, for a particular ethanol recovery process, it is desirable to reduce the quantity of biomass in order to reduce the load of solids on the sedimentation, centrifugation or filtration apparatus.

At the same time, however, the yield of ethanol from the fermentation must be maximized. Since product formation cannot occur in the absence of biomass, ethanol formation is dependent on cell mass concentration. In fact, the rate of ethanol production in the fermenter is directly proportional to the quantity of biomass in the fermenter under steady state conditions. Thus, within the limits of the metabolic regulatory controls of the microorganism and process dynamics, increasing the biomass in the fermenter while maintaining other conditions constant will shorten the time required to produce a given amount of ethanol. However, this seemingly simple approach for optimizing process performance will have an adverse effect on the ethanol recovery process because the load of solids on the separating equipment will be correspondingly increased.

It is well known that the substrate, such as glucose, is the largest item of raw material cost in the fermentation. Therefore, the presence of substrate in the effluent from the fermenter in a continuous fermentation is to be avoided. The continuous fermentation should be conducted at optimum process product yield, which occurs when the substrate is completely converted to ethanol and when the substrate is minimally diverted from product (ethanol) formation to cell mass synthesis (i.e., when the growth yield with respect to carbon substrate is minimized).

Thus, there exists a need in the art for a continuous process for the production of ethanol using strains of Zymomonas in which the substrate fed to the fermenter is converted to ethanol in as short a time as possible. The process should permit a reduction in the quantity of biomass in the fermenter in order to obtain a corresponding reduction in the load of solids on the ethanol recovery apparatus. In addition, the quantity of substrate in the effluent from the fermenter should be minimized.

SUMMARY OF THE INVENTION

This invention aids in fulfilling these needs in the art by providing a continuous process for the production of ethanol. The present invention relates to an improvement in the fermentation performance of strains of Zymomonas in continuous fermentations wherein metabolic processes are limited by various nutrients, these nutrients being nitrogen, potassium or phosphorus. When growth is limited by one of these nutrients, the biomass expresses its maximum value for both specific rate of substrate uptake ($q_s$) and specific rate of product formation ($q_p$) at any given value of dilution rate (D) and substrate concentration ($S_r$). One of the criteria for assessing the improvement in performance of Zymomonas according to this invention is the increase in the specific rate of ethanol (product) formation ($q_p$). The response of Zymomonas with respect to nutrient limitation by nitrogen, potassium or phosphorus could not be predicted from prior teachings. That Zymomonas expresses a maximal value for $q_p$ (and $q_s$) under conditions of nutrient limitation was not a predictable phenomenon. The process of this invention is conducted at a lower biomass concentration and a higher specific rate of ethanol formation than a similar process conducted with a nutrient medium that contains the nutrient in excess.

In one embodiment of this invention, a method of improving continuous ethanol production by bacterial fermentation with strains of Zymomonas is provided without changing the fermentation temperature. These results are achieved by carrying out the fermentation under nutrient-limiting conditions. The limiting nutrient is either nitrogen, potassium or phosphorus. The imposition of nutrient limitation makes it possible to conduct the fermentation at a lower biomass concentration at a given substrate concentration in the feed stream to the fermenter or at a given dilution rate than under conditions of nutrient-excess. Consequently, for a given substrate concentration in the feed stream to the fermenter or a given dilution rate, the fermenter can be operated at a higher specific rate of product formation under the nutrient-limiting conditions than under the nutrient-excess conditions. Moreover, as the concentration of substrate in the feed stream is increased or as the dilution rate is increased, the biomass in the fermenter also increases, but the biomass level is less under nutrient-limiting conditions than under conditions of nutrient-excess. Furthermore, nutrient-limitation does not appreciably affect product yield ($Y_{p/s}$ can be increased in some instances) when compared with a similar fermentation carried out under nutrient-excess; the yield at a given substrate concentration in the feed stream or a given dilution rate is substantially the same under nutrient-limiting conditions as under nutrient-excess conditions. In addition, product yield is substantially unaffected under nutrient-limiting conditions when either the concentration of substrate in the feed stream or the dilution rate is increased. At the same time, substantially all the substrate is converted to ethanol; unconverted substrate in the effluent can be avoided.

The amount of the limiting nutrient in the culture medium required to achieve nutrient-limited fermentation according to this invention is proportional to the concentration of substrate in the feed stream to the fermenter and to the dilution rate. In order to maintain a specific rate of product formation, the amount of the limiting nutrient in the fermentation medium must be increased as the concentration of substrate in the feed stream is increased. Similarly, when the dilution rate is increased, the amount of limiting nutrient in the fermentation medium must be increased to maintain the specific rate of product formation.

In a situation where high cell density is artificially maintained, such as in a single-stage recycle system, a higher overall productivity could be maintained with the nutrient-limited fermentation of this invention. In such a system, the upper limit to the productivity of the fermenter is often determined by the capacity of the recycle device to handle a maximum biomass load. Nutrient limitation results in a reduction in the biomass level without significantly altering the capacity of the fermenter to handle the same substrate load.

In another embodiment of this invention, a method of improving performance of Zymomonas in continuous ethanol fermentation at increased temperatures has now been discovered. It has surprisingly been found that the specific rate of substrate uptake can be maintained, and even increased, at fermentation temperatures of about 33° C. to about 37° C. even though there is a lower biomass concentration in the fermenter. These results can be achieved without substantial amounts of substrate in the effluent from the fermenter. These advantages have a positive impact on product recovery and process economics. These results are achieved with this invention by carrying out continuous ethanol fermentation with Zymomonas strains under nutrient-limited conditions, where the limiting nutrient is nitrogen, potassium or phosphorus. The concentration of the limiting nutrient in the fermentation medium is increased with increasing temperature and decreased with decreasing temperature.

BRIEF DESCRIPTION OF THE DRAWING

The FIGURE is a schematic drawing of fermentation apparatus of the type that can be employed in practicing the process of this invention.

DETAILED DESCRIPTION

The accompanying FIGURE will provide a background for the following discussion in which the method and apparatus for carrying out this invention are described in detail. Referring to the FIGURE, nutrient medium 1 in reservoir 2 is fed by a pump 3 to a fermenter 4 containing a fermentation medium 5. The medium is maintained at a constant volume in the fermenter by means of an overflow weir 6 that empties into a container 7. Carbon dioxide formed during the fermentation is vented at 8.

The fermenter 4 is provided with an agitator 9 for mixing the fermenter contents. A pH probe 10 is immersed in the fermentation medium 5 and is connected to a pH controller 11 for regulating the amount of pH regulating agent 12 in reservoir 13 added by a pump 14 to the fermentation medium 5.

The temperature of the fermentation medium is monitored by temperature probe 15. The fermentation medium is heated or cooled as required through a coil 16 and regulated by the temperature controller 17.

The fermentation medium is formulated so that all but a single essential nutrient are available in excess of the amount required to synthesize a desired cell concentration. The single growth-limiting nutrient controls the size of the steady-state cell population.

Conventional expressions are used throughout this description when the kinetics of the fermentation process are discussed. The abbreviations identified in the following list have been used in order to facilitate the discussion. Units of measure have been included where appropriate.

$S_r$ = Substrate concentration in the feed stream to the fermenter; g/liter, i.e. g/L.
$S_o$ = Substrate concentration in the effluent from the fermenter; g/L.
V = Volume of fermentation medium in the fermenter; L.
X = Concentration of biomass in the fermentation medium (dry basis); g/L.
[P] = Concentration of ethanol in the fermentation medium; g/L.
u = Specific growth rate (mass); $hr^{-1}$.
D = Dilution rate; $hr^{-1}$.
N* = Amount of a given nutrient; g.
$q_s$ = Specific rate of substrate uptake; g substrate/g biomass-$hr^{-1}$.
$q_s^{max}$ = Maximum observed specific rate of substrate uptake; g substrate/g cell-$hr^{-1}$.
$q_p$ = Specific rate of ethanol formation; g ethanol/g biomass-$hr^{-1}$.
$q_p^{max}$ = Maximum observed specific rate of ethanol formation; g ethanol/g cell-$hr^{-1}$.
VP = Volumetric Productivity; g ethanol/L-$hr^{-1}$.
$Y_n$ = Growth yield coefficient for a specified limiting nutrient, n; g dry biomass/g-atom nutrient.
n = Limiting nutrient, i.e., nitrogen, potassium or phosphorus.
$Y_{p/s}$ = Product Yield Coefficient = $q_p/q_s$; g ethanol produced/g substrate consumed.
$Y_{x/s}$ = Growth yield coefficient; g biomass/g-atom of substrate consumed.

YE=yeast extract (Difco) in aqueous medium; g/L.
AC=High grade anhydrous NH$_4$Cl in aqueous solution; g/L.
AS=High grade anhydrous (NH$_4$)$_2$SO$_4$ in aqueous solution; g/L.
Eth=ethanol
Glu=glucose

NUTRIENT-LIMITED FERMENTATION

As used herein, the expression "nutrient-limited fermentation" and similar expressions mean a fermentation of an organic substrate by a Zymomonas strain, where the fermentation is carried out in a continuous process under steady-state conditions in a medium in which one or more nutrients are present in an amount such that the rate of growth is limited by the availability of one or more of the essential nutrients.

As used herein the expression "limiting nutrient" means nitrogen, potassium or phosphorus.

The process of this invention is carried out as a continuous fermentation. The term "continuous" is used in its conventional sense and means that nutrients are fed to a fermenter substantially continuously and that an output, or effluent, stream is substantially constantly withdrawn from the fermenter. The nutrient stream usually comprises an aqueous organic substrate solution. The effluent stream comprises biomass and the liquid phase from the fermentation medium.

Fermentation can be carried out in a bioreactor, such as a chemostat, tower fermenter or immobilized-cell bioreactor. Fermentation is preferably carried out in a continuous-flow stirred tank reactor. Mixing can be supplied by an impeller, agitator or other suitable means and should be sufficiently vigorous that the vessel contents are of substantially uniform composition, but not so vigorous that the microorganism is disrupted or metabolism inhibited.

Fermentation is carried out with a submerged culture and under substantially anaerobic conditions. While the invention is described in the Examples hereinafter with freely mobile cells, it will be understood that immobilized cells can also be employed. The fermenter is preferably enclosed and vented to allow the escape of carbon dioxide evolved during the fermentation. Oxygen at the surface of the fermentation medium is to be avoided. This may inherently occur as the heavier carbon dioxide evolved during the fermentation displaces the oxygen in the gas phase above the medium. If necessary, the gas phase above the medium can be purged with an inert gas to remove oxygen and maintain substantially anaerobic conditions.

The fermenter can be operated with or without cell recycle. Cell recycle makes it possible to increase the productivity of the system by operating at a higher steady-state cell concentration compared to a similar system without cell recycle. When cell recycle is employed, a portion of the fermenter contents is withdrawn from the fermenter, the ethanol-containing phase is separated from the effluent, and the resulting concentrated cells are returned to the fermenter. The separation is typically carried out by microfiltration or centrifugation. Since the process of this invention is carried out at reduced biomass concentration in the fermenter, the load of solids on the cell recycle apparatus is reduced and ease of ethanol recovery is increased.

The composition of the effluent stream can vary and will usually be the same as the composition of the fermentation medium. When a flocculent strain of Zymomonas is employed, however, or if partial separation of biomass from the liquid phase otherwise occurs in the fermenter, the effluent can contain a larger proportion of biomass or liquid phase depending upon the location where the effluent is withdrawn from the fermenter.

The microorganism employed in the process of this invention is a gram-negative, facultative anaerobic bacterium of the genus Zymomonas capable of fermenting an organic substrate to ethanol under substantially anaerobic continuous culture conditions. Typical strains are *Zymomonas mobilis* and *Zymomonas anaerobia*. Suitable strains of Zymomonas are available from microorganism depositories and culture collections. Examples of suitable *Z. mobilis* strains are those identified as ATCC 10988, ATCC 29191, ATCC 31821 and ATCC 31823 [ex ATCC 31821]. Examples of other strains of *Z. mobilis* are those identified as NRRL B-14023 [CP 4] and NRRL B-14022 [CP 3]. Flocculent strains can also be employed. These strains include ATCC 35001 [ex ATCC 29191], ATCC 35000 [ex NRRL B-14023], ATCC 31822 [ex ATCC 31821], and NRRL B-12526 [ex ATCC 10988]. *Z. mobilis* strains are occasionally referred to in the literature by the following alternate designations:

TABLE 1

| Culture Collection Accession No. | Literature Designation |
| --- | --- |
| ATCC 10988 | Strain ZM 1 |
| ATCC 29191 | Strain ZM 6 (or Z6) |
| ATCC 31821 | Strain ZM 4 |
| ATCC 31822 | Strain ZM 401 |
| ATCC 31823 | Strain ZM 481 |
| NRRL B-14022 | Strain CP3 |
| NRRL B-14023 | Strain CP4 |

It will be understood that other Zymomonas strains can be obtained by selective cultivation or mutation as well as by genetic engineering techniques to provide microorganisms with desired metabolic properties.

The substrate employed in the process of this invention is an organic, fermentable substrate for Zymomonas strain. As the carbon source for both the growth and fermentation stages of the process, various carbohydrates can be employed. Examples of suitable carbohydrates are sugars, such as glucose, fructose and sucrose; molasses; starch hydrolysates; and cellulose hydrolysates. Other suitable substrates will be apparent to those skilled in the art. The organic substrate can be employed either singly or in admixture with other organic substrates.

The substrate is fed to the fermenter in aqueous solution. The concentration of organic substrate in the fermentation medium will depend upon the culture conditions. The substrate is employed in an amount sufficient for cell growth and product formation. Typically, the concentration of fermentable substrate in the feed stream to the fermenter will be about 100 to about 180 g/L.

The flow rate of the substrate solution to the fermenter will depend upon the size and configuration of the fermenter, the amount of biomass in the fermenter and the rate at which substrate is consumed, and can be determined with a minimum of experimentation. The flow rate should be below the rate at which a substantial amount of substrate appears in the effluent from the fermenter. Preferably, the flow rate of the substrate solution to the fermenter should be such that the effluent substrate concentration is less than about 5% $S_f$, and should be such that the effluent is substantially free of substrate under optimum operating conditions.

The process of this invention can be carried out over a moderate range of temperatures. The effects of temperature changes on fermenter performance are discussed below, but generally speaking, the process of this invention is carried out at a temperature of about 27° C. to about 37° C., preferably about 30° C.

Zymomonas fermentations have been reported at pH values ranging from about 4 to about 8 in the culture medium. The process of this invention can be carried out over a moderate range of pH values in the culture medium, but rapid metabolism of the organic substrate with high product yield occurs over a narrower range. The process of this invention is preferably carried out at a pH of about 4.5 to about 6.5. At pH values above about 6.5, product yield decreases and the formation of undesirable products increases. The particularly preferred pH is about 5.5, which was the pH used in all of the fermentations described herein.

The pH in the culture medium often falls and rises during the fermentation. To restrict pH changes during fermentation, the medium can be buffered. In addition, the pH of the medium can be intermittently or continuously monitored and acidic or basic substances added to adjust pH during the course of fermentation. A buffering agent or a pH regulating agent that is non-toxic and substantially non-inhibitory to the microorganism can be employed for this purpose. The pH regulating agent is typically a hydroxide or an organic or inorganic acid. Examples of suitable pH regulating agents are potassium hydroxide, sodium hydroxide and hydrochloric acid.

The process of this invention is carried out under sufficiently sterile conditions to ensure cell viability and metabolism. This requires careful selection of the microorganism, sterilization of the apparatus for the fermentation and of the liquid and gaseous streams fed to the fermenter. Liquid streams can be sterilized by several means, including radiation, filtration and heating. Small amounts of liquids containing sensitive vitamins and other complex molecules can be sterilized by passage through microporous membranes. Heat-treatment processes are preferred for sterilizing the substrate feed stream and can be carried out by heating the stream in a batch or continuous flow vessel. The temperature must be high enough to kill essentially all organisms in the total holding time. Water utilized in the preparation of the substrate solution and in the preparation of the fermentation broth in the fermenter can be sterilized in a similar manner or by other conventional techniques.

After the fermenter has been inoculated with the Zymomonas microorganism, the quantity of biomass is multiplied. The growing culture is allowed to complete the lag phase and substantially the entire exponential phase of growth before flow to the fermenter is initiated. The fermentation is allowed to proceed under substantially steady state conditions with the continuous introduction of fresh substrate and the continuous withdrawal of product from the fermenter. While product formation is not solely associated with growth, it will be understood that a portion of the substrate fed to the fermenter goes into cell maintenance. Thus, in the case of direct conversion of glucose to ethanol

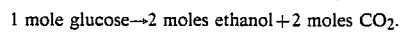

1 mole glucose→2 moles ethanol+2 moles $CO_2$.

The maximum conversion is 2 mole ethanol per mole glucose or 0.51 g ethanol/g glucose, but theoretical yield cannot be achieved in practice since some of the substrate goes into cell mass. The process of this invention is carried out at a yield of at least about 80%, preferably at least about 94%, of theoretical yield. Complete conversion is about 95% or more.

Viable cell concentration in the fermenter will depend upon several factors, such as dilution rate, substrate concentration, maximum growth rate and growth yield coefficient. The fermenter can be operated over a range of biomass concentrations and the optimum concentration can be determined without undue experimentation. The practical range of values will generally depend upon process economics. For example, a continuous chemostat culture without cell recycle at maximum substrate concentration in the feed stream can typically be operated at a maximum biomass concentration of about 3.5 g/L. A practical range of biomass concentrations is about 0.8 to about 3.2 g/L.

The concentration of ethanol in the fermentation medium should be maximized in order to reduce the cost of product recovery. The process of this invention is carried out at ethanol concentrations up to about 85 g/L, preferably about 28 g/L to about 70 g/L, especially about 50 g/L to about 60 g/L, in the fermentation medium.

Z. mobilis is sensitive to ethanol concentration, and at concentrations in excess of about 50 g/L (5% w/v), cell growth and metabolism are retarded. This can be caused by a high concentration of substrate in the feed stream to the fermenter. Thus, as the value for $S_r$ is increased, the maximum dilution rate for substantially complete conversion of substrate to ethanol should be decreased. The process of this invention is carried out at a dilution rate of about 0.05 $hr^{-1}$ to about 0.35 $hr^{-1}$, preferably about 0.1 $hr^{-1}$ to about 0.2 $hr^{-1}$.

These features of this invention will be more fully understood from the following discussion. The effects of the limiting nutrient on fermenter performance at various concentrations of substrate in the feed stream and different dilution rates are summarized below. The results obtained in a series of experiments with varying operating conditions are reported in the following Tables.

NITROGEN-LIMITED FERMENTATION

Table 2 shows the effect of increasing the concentration of glucose in the feed stream on the performance of a continuous fermentation by Z. mobilis strain ATCC 29191 in a chemostat at a constant dilution rate of 0.15 $hr^{-1}$ under either nitrogen-limiting conditions or conditions of nitrogen-excess. The amount of assimilable nitrogen was varied by changing the amount of either yeast extract (YE), ammonium chloride (AC) or ammonium sulphate (AS). The amount of the nitrogen-limiting additive was the minimal amount required to achieve maximal rate of sugar utilization and ethanol production by the Z. mobilis strain udner the fermentation conditions.

TABLE 2

Amount of Assimilable Nitrogen as either Yeast Extract (Difco), Ammonium Chloride or Ammonium Sulphate Required to Achieve Maximal Rate of Sugar Utilization and Ethanol Production by *Z. mobilis* ATCC 29191 in Continuous Culture at Fixed Dilution Rate (0.15 hr$^{-1}$) as a Function of Feed Sugar Concentration ($S_r$)

| | | Excess Nitrogen | | | Nitrogen Limitation | | | | | |
|---|---|---|---|---|---|---|---|---|---|---|
| $S_r$ g/L | [P] g/L | X g/L | $q_s$ | $q_p$ | X g/L | $q_s$ | $q_p$ | YE g/L | AC g/L | AS g/L |
| 20 | 9.6 | 0.58 | 5.2 | 2.5 | 0.36 | 8.3 | 3.9 | 0.8 | 0.19 | 0.23 |
| 60 | 28 | 1.73 | 5.2 | 2.5 | 1.1 | 8.3 | 3.9 | 2.4 | 0.59 | 0.72 |
| 110 | 52 | 3.17 | 5.2 | 2.5 | 2.0 | 8.3 | 3.9 | 4.4 | 1.10 | 1.32 |

Units: $q_s$ = g glu/g cell·hr$^{-1}$; $q_p$ = g eth/g cell·hr$^{-1}$.

The data in Table 2 show that a fermenter can be operated according to this invention at a lower biomass concentration under nitrogen-excess at a given glucose concentration. For example, with a glucose concentration ($S_r$) of 20 g/L in the feed stream, the biomass concentration (X) in the fermenter was only 0.36 g/L under nitrogen-limiting conditions, whereas the biomass concentration was 0.58 g/L under conditions of nitrogen-excess. A similar comparison can be made for the other glucose concentrations shown in Table 2.

The data in Table 2 also show that the fermenter can be operated at a higher specific rate of product formation ($q_p$) under nitrogen-limiting conditions than under conditions of nitrogen-excess at a given glucose concentration. The observed specific rate of product formation of 3.9 under nitrogen-limiting conditions was approximately 1.56 times greater than observed $q_p$ under conditions of nitrogen-excess.

In addition, the data in Table 2 demonstrate that as the concentration of glucose in the feed stream ($S_r$) is increased, biomass concentration (X) also increases under both nitrogen-limiting and nitrogen-excess conditions, but the biomass level is less under nitrogen-limiting conditions than under conditions of nitrogen-excess for a given $S_r$.

For near complete conversion of glucose to ethanol, the amount of limiting nitrogen was increased as the glucose concentration was increased. For example, in order to achieve complete fermentation of added substrate, the quantity of yeast extract in the nutrient medium was increased from 0.8 g/L to 4.4 g/L when the glucose concentration in the feed stream was increased from 20 g/L to 110 g/L. The culture expressed maximal values for $q_p$ and $q_s$ under these conditions. These results were entirely unexpected.

The data in Table 2 also show that nitrogen-limitation in the fermentation medium does not appreciably affect product yield when compared with a similar fermentation carried out under conditions of nitrogen-excess. The product yield was about 92% of the theoretical maximum yield in all cases. [[e.g., [28/(60×0.51)]×100=92%]]. These results were also entirely unexpected.

Another series of fermentations similar to those summarized in Table 2 was carried out, except that the concentration of glucose in the feed stream ($S_r$) to the fermenter was maintained at 110 g/L while the dilution rate (D) was varied. Table 3 shows the amount of assimilable nitrogen as either yeast extract (YE), ammonium chloride (AC) or ammonium sulphate (AS) required to achieve maximal rate of sugar utilization and ethanol production under nitrogen-limiting conditions and conditions of nitrogen-excess.

TABLE 3

Amount of Assimilable Nitrogen as either Yeast Extract (Difco) Ammonium Chloride or Ammonium Sulphate Required to Achieve Maximal Rate of Sugar Utilization and Ethanol Production by *Z. mobilis* ATCC 29191 in Continuous Culture at Fixed Feed Glucose Concentration ($S_r$ = 110 g/L) as a Function of the Dilution Rate (D)

| | | Excess Nitrogen | | | Nitrogen Limitation | | | | | | |
|---|---|---|---|---|---|---|---|---|---|---|---|
| D hr$^{-1}$ | $S_r$ g/L | X g/L | $q_s$ | $q_p$ | X g/L | $q_s$ | $q_p$ | YE g/L | AC g/L | AS g/L | $S_o$ g/L |
| 0.1 | 110 | 2.53 | 4.4 | 2.1 | 1.33 | 8.3 | 3.9 | 3.0 | 0.71 | 0.88 | 5 |
| 0.15 | 110 | 3.17 | 5.2 | 2.5 | 2.00 | 8.3 | 3.9 | 4.4 | 1.07 | 1.32 | 5 |
| 0.2 | 110 | 3.63 | 6.1 | 2.9 | 2.65 | 8.3 | 3.9 | 5.9 | 1.42 | 1.74 | 5 |
| 0.2 | 110 | | | | 2.00 | 8.3 | | | 1.07 | | 30 |

Units: $q_s$ = g glu/g cell·hr$^{-1}$; $q_p$ = g eth/g cell·hr$^{-1}$.

The data in Table 3 demonstrate that a fermenter can be operated according to this invention at a lower biomass concentration under nitrogen limiting conditions than under conditions of nitrogen-excess at a given dilution rate. The fermenter can be operated at a higher specific rate of product formation under nitrogen-limiting conditions than under conditions of nitrogen-excess at a given dilution rate. As the dilution rate is increased, biomass concentration in the fermenter also increases with increasing amounts of nitrogen, but the biomass level is less under nitrogen-limitation than under nitrogen-excess.

The amount of assimilable nitrogen required for nitrogen-limited fermentation is proportional to the dilution rate and must be increased as the dilution rate is increased to achieve complete substrate conversion to ethanol. The significance of this feature of the invention can be more fully appreciated by comparing the data in Table 3. When the fermentation was carried out under nitrogen-limiting conditions and the dilution rate was doubled, say from 0.1 hr$^{-1}$ to 0.2 hr$^{-1}$, the amount of ammonium chloride (AC), or its equivalent, had to be about doubled, e.g., from 0.71 to 1.42, in order to ensure substantially complete fermentation of the glucose substrate. By comparison, when the amount of assimilable nitrogen as ammonium chloride was maintained at 1.07 g/L while the dilution rate was increased 0.15 hr$^{-1}$ to 0.2 hr$^{-1}$, the biomass concentration in the fermenter remained constant at 2.00 g/L, but the fermentation was incomplete as evidenced by the appearance of unfermented glucose in the fermenter effluent. The glucose concentration in the effluent ($S_o$) increased from a level of less than 0.5% (w/v) to a level of about 3.0% (w/v) when the concentration of assimilable nitrogen was not adequately controlled.

Nitrogen limitation according to this invention does not appreciably affect the efficiency of conversion of substrate to ethanol, expressed as the amount of ethanol produced per amount of substrate utilized, rather than the amount of ethanol produced per the amount of substrate added to the fermenter. In the fermentations reported in Table 3 that were carried out according to this invention, the observed ethanol concentration was about 52 g/L. This corresponded to a product yield of about 93% of the theoretical maximum yield.

Under conditions of excess-nitrogen, the specific rate of glucose uptake and the specific rate of ethanol production increases with increasing dilution rates. In the case of nutrient-limited fermentation, the biomass expresses maximal rate of sugar uptake and maximal rate of ethanol production. The rates are higher in all cases with nutrient-limitation than with nutrient-excess. The data in Table 3 show that a more pronounced effect on the specific rate of glucose uptake and the specific rate of product formation can be obtained at lower dilution rates by carrying out the fermentation under nitrogen-limiting conditions according to this invention.

Data demonstrating that there is typically a maximum imposed on both the concentration of glucose in the feed stream ($S_r$) to the fermenter and the dilution rate (D) when complete conversion (95% or more) of sugar to ethanol is desired at relatively high ethanol concentrations can be found in Table 4.

TABLE 4

Amount of Assimilable Nitrogen as Either Yeast Extract (Difco) Ammonium Chloride or Ammonium Sulphate Require to Achieve Maximal Rate of Sugar Utilization and Ethanol Production by Z. mobilis ATCC 29191 at High Product Concentration $D = 0.08\ hr^{-1}$

| | | Excess Nitrogen | | | Nitrogen Limitation | | | | | |
|---|---|---|---|---|---|---|---|---|---|---|
| $S_r$ g/L | Eth g/L | X g/L | $q_s$ | $q_p$ | X g/L | $q_s$ | $q_p$ | YE g/L | AC g/L | AS g/L |
| 150 | 67 | 2.16 | 5.1 | 2.4 | 1.37 | 8.3 | 3.9 | 3.1 | 0.73 | 0.90 |

Units: $q_s$ = g glu/g cell-$hr^{-1}$; $q_p$ = g product/g cell-$hr^{-1}$.

When the concentration of glucose in the feed stream was elevated to 150 g/L, the maximum dilution rate that could be maintained for complete fermentation was $0.08\ hr^{-1}$. The ethanol concentration in the fermentation medium was 67 g/L for this glucose level. Table 4 compares the results for nitrogen-limited fermentation according to this invention with fermentation carried out under conditions of nitrogen-excess. The data show that even with a high concentration of sugar in the feed stream and a high ethanol concentration in the fermentation medium, this invention makes it possible to operate at a reduced biomass level, an increasd rate of substrate uptake and an increased rate of product formation.

POTASSIUM-LIMITED FERMENTATION

This invention can also be carried out by potassium-limited fermentation of Zymomonas in continuous culture in a manner analogous to the nitrogen-limited fermentation previously described and with comparable results. The range of tolerable amounts of potassium in the nutrient medium is rather narrow. For this reason, and for the additional reason that the amount of the limiting nutrient must be known with substantial precision, potassium-limited fermentation is conducted in a defined salts medium. An example of a suitable medium is described hereinafter with reference to Table 7.

The amount of potassium, as potassium chloride, required to achieve maximum rate of sugar utilization and ethanol production by Z. mobilis strain ATCC 29191 in continuous culture in a chemostat at fixed dilution rate of $0.15\ hr^{-1}$ was determined as a function of feed sugar concentration. The results are reported in Table 5.

TABLE 5

Amount of Potassium (as Potassium Chloride) Required to Achieve Maximal Rate of Sugar Utilization and Ethanol Production by Z. mobilis ATCC 29191 in Continuous Culture at Fixed Dilution Rate ($0.15\ hr^{-1}$) as a Function of Feed Sugar Concentration $D = 0.15\ hr^{-1}$

| | | Excess Potassium | | | Potassium Limitation | | | |
|---|---|---|---|---|---|---|---|---|
| $S_r$ g/L | Eth g/L | X g/L | $q_s$ | $q_p$ | X g/L | $q_s$ | $q_p$ | KCl g/L |
| 20 | 9.6 | 0.58 | 5.2 | 2.5 | 0.40 | 7.5 | 3.6 | 0.024 |
| 60 | 28 | 1.73 | 5.2 | 2.5 | 1.2 | 7.5 | 3.6 | 0.071 |
| 110 | 52 | 3.17 | 5.2 | 2.5 | 2.2 | 7.5 | 3.6 | 0.129 |

Units: $q_s$ = g glu/g cell-$hr^{-1}$; $q_p$ = g eth/g cell-$hr^{-1}$.

As shown in Table 5 and as in the nitrogen-limited fermentation, potassium-limited fermentation can be carried out at lower biomass concentration than under conditions of potassium-excess at a given glucose concentration. Also, the fermenter can be operated at a higher $q_p$ under potassium-limitation than under potassium-excess at a given glucose concentration. As glucose in the feed is increased, biomass in the fermenter also increases, but the biomass level is less under potassium-limitation than under potassium-excess. As with nitrogen-limited fermentation, the amount of potassium required for potassium-limited fermentation is proportional to the concentration of glucose in the feed stream; the amount of potassium as KCl must be increased as glucose concentration is increased to maintain $q_p$. Once again, the nutrient limitation does not appreciably affect product yield when compared with a similar fermentation carried out under nutrient-excess.

When this invention is carried out with potassium-limited fermentation and when it is necessary to control the pH of the fermentation medium, a pH regulating agent or buffering agent other than potassium hydroxide or other potassium-containing compound should be employed, otherwise it is practically impossible to control the amount of potassium in the fermentation medium. The use of sodium hydroxide as the pH regulating agent in a potassium-limited fermentation has been found to be advantageous. Sodium apparently acts as a potassium antagonist, and the resulting elevated level of sodium after the addition of sodium hydroxide to the fermenter potentiates the effect of potassium-limitation on the specific activity of the biomass. A buffering agent, such as $NaH_2PO_4$, can also be employed.

PHOSPHORUS-LIMITED FERMENTATION

This invention can be carried out by phoshorus-limited fermentation of Zymomonas in continuous culture in a manner analogous to the nitrogen-limited fermentation previously described and with comparable results. As with potassium-limited fermentation, the range of tolerable amounts of phosphorus in the nutrient medium is rather narrow. For this reason, and for the additional reason that the amount of the limiting element must be known with substantial precision, phosphorus-limited fermentation is conducted in a defined salts medium. Once again, an example of a suitable medium is described hereinafter with reference to Table 7.

The amount of assimilable phosphorus as potassium dihydrogen phosphate required to achieve maximal rate of sugar utilization and ethanol production by Zymomonas mobilis strain ATCC 29191 in continuous culture in a chemostat at fixed dilution rate of $0.15\ hr^{-1}$ was determined as a function of feed sugar concentration. The amount of potassium dihydrogen phosphate employed and the results obtained are reported in Table 6.

TABLE 6

Amount of Assimilable Phosphorus, as $KH_2PO_4$, Required to Achieve Maximal Rate of Sugar Utilization and Ethanol Production by *Z. mobilis* ATCC 29191 in Continuous Culture at Fixed Dilution Rate (0.15 hr$^{-1}$) as a Function of Feed Sugar Concentration $D = 0.15$ hr$^{-1}$

| | | Excess Phosphate | | | Phosphate Limitation | | | |
|---|---|---|---|---|---|---|---|---|
| $S_r$ g/L | Eth g/L | X g/L | $q_s$ | $q_p$ | X g/L | $q_s$ | $q_p$ | $KH_2PO_4$ g/L |
| 20 | 9.6 | 0.58 | 5.2 | 2.5 | 0.42 | 7.2 | 3.4 | 0.04 |
| 60 | 28 | 1.73 | 5.2 | 2.5 | 1.25 | 7.2 | 3.4 | 0.13 |
| 110 | 52 | 3.17 | 5.2 | 2.5 | 2.29 | 7.2 | 3.4 | 0.23 |

Units: $q_s$ = g glu/g cell·hr$^{-1}$; $q_p$ = g eth/g cell·hr$^{-1}$.

The data in Table 6 show that the results obtained with phosphorus-limited fermentation are analogous to the results obtained with nitrogen-limited and potassium-limited fermentations. Phosphorus-limited fermentation can be carried out at lower biomass concentration, higher specific rate of glucose uptake, higher specific rate of product formation and comparable product yield as compared to fermentation carried out under conditions of phosphorus-excess. The data show that the amount of phosphorus required for phosphorus-limited fermentation is proportional to the concentration of glucose in the feed stream.

When this invention is carried out with phosphorus-limited fermentation and when it is necessary to control the pH of the fermentation medium, a pH regulating agent or buffering agent other than a phosphorus-containing compound should be employed. The additional source of phosphorus from a phosphorus-containing pH regulating agent may prevent the degree of control of nutrient-limitation required by the invention. For phosphorus-limited fermentation $KH_2PO_4$ can be employed as a buffer and NaOH titrant diluted to 0.5N in order to avoid large changes in pH during automatic titration.

FORMULATING THE NUTRIENT MEDIUM

The identity of the chemical constituents in the nutrient medium and the amount of each constituent should be sufficient to meet the elemental requirements for cell mass and ethanol production and should supply appropriate energy for synthesis and maintenance. The nutrient medium should contain carbon, nitrogen, potassium, phosphorus, sulfur, magnesium, calcium and iron in required amounts. The chemical constituents should also meet specific nutrient requirements including vitamins and trace minerals.

As the assimilable source of nitrogen, various kinds of inorganic or organic salts or compounds can be included in the nutrient medium. For example, ammonium salts, such as ammonium chloride or ammonium sulfate, or natural substances containing nitrogen, such as yeast extract, peptone, casein hydrolysate or corn steep liquor, or amino acids, such as glutamic acid, can be employed. These substances can be employed either singly or in combination of two or more.

Examples of inorganic compounds that can be included in the culture medium are magnesium sulfate, potassium monohydrogen phosphate, potassium dihydrogen phosphate, sodium chloride, magnesium sulfate, calcium chloride, iron chloride, magnesium chloride, sinc sulfate, cobalt chloride, copper chloride, borates and molybdates.

Organic compounds that may be desirable in the fermentation include, for example, vitamins, such as biotin, calcium pantothenate, and the like, or organic acids, such as citric acid, or amino acids, such as glutamic acid. It has been found, however, that biotin is not required in the growth medium.

Fermentation aids that are non-toxic to the microorganism can be included in the nutrient medium and fermentation broth. For example, an anti-foaming agent in a minor amount has been found to be advantageous.

Examples of nutrient media that have been found suitable for use in this invention are described in Table 7.

TABLE 7

Chemical Composition of Growth Media for Continuous Culture of *Z. mobilis*

| INGREDIENT | SEMI-SYNTHETIC MEDIUM (g/L) | DEFINED SALTS MEDIUM (g/L) |
|---|---|---|
| D-Glucose (anhydrous) approx. | 100 | 100 |
| Yeast Extract (Difco) | 5 | — |
| $NH_4Cl$ | 2.4 | 2.4 |
| $KH_2PO_4$ | 3.48 | 3.48 |
| $MgSO_4 \cdot 7H_2O$ | 1.0 | 1.0 |
| $FeSO_4 \cdot 7H_2O$ | 0.01 | 0.01 |
| Citric Acid | 0.21 | 0.21 |
| Vitamins | | |
| Ca-pantothenate | 0.001 | 0.001 |
| Biotin | 0.001 | 0.001 |
| Antifoam as required | | |

The semi-synthetic medium is suitable for use in the nitrogen-limited fermentation according to this invention. It will be understood that the composition of this medium will depend on the technical quality of the nitrogen source. For example, yeast extract from a batch from one commercial source may exhibit a different potency with respect to the content of assimilable nitrogen than a yeast extract from a different batch or from another commercial source. Also, the amount of the nitrogen source required in the medium will depend on the degree of hydration; anhydrous chemicals are preferred and were employed in the Examples and in the fermentations reported in the Tables.

The defined salts medium is suitable for use in carrying out the potassium-limited and phosphorus-limited fermentations. Only inorganic sources of nitrogen, such as ammonium salts, are employed in defined salts media. In the experiments reported in the foregoing Tables and Examples, the defined salts medium was used in the potassium- and phosphorus-limited fermentations, with the following exceptions.

Ordinarily, the phosphorus in the nutrient medium is supplied as a salt having an anion that is substantially non-toxic to the microorganism and that does not substantially inhibit normal metabolic processes. While a potassium salt, such as potassium dihydrogen phosphate, is typically employed for nitrogen-limited and phosphorus-limited fermentations, a sodium salt is preferably substituted for the potassium salt in potassium-limited fermentation. For example, sodium dihydrogen phosphate instead of potassium dihydrogen phosphate can be utilized. Since the amount of available potassium must be precisely known under potassium-limited conditions, this substitution makes it easier to control the relative proportions of nutrients.

The potassium in the nutrient medium for potassium-limited fermentation is supplied by a salt having an anion that is substantially non-toxic to the microorganism and that does not substantially inhibit normal metabolic processes. The source of potassium is preferably potassium chloride, although similar water-soluble, inorganic salts can be employed.

The amount of limiting nutrient in the nutrient medium mainly depends on two factors: The concentration of substrate in the feed stream to the fermenter and the dilution rate. As the substrate concentration at a constant dilution rate is increased, the amount of limiting nutrient is increased. Similarly, at a constant substrate concentration, the amount of limiting nutrient is increased as the dilution rate increases. These relationships apply to nitrogen-limited, potassium-limited and phosphorus-limited fermentations, since the fermentations are analogous to each other. The concentrations of inorganic salts other than the N-, K- and P-containing salts are relatively invariant with the formulations shown in Table 7.

The nutrient media in Table 7 can also be employed in a fermentation carried out under conditions of nutrient excess. For example, a nitrogen-excess medium based on yeast extract (Difco) and ammonium ion can contain about 5 to about 10 g/L of the yeast extract and about 15 to about 34 mM, preferably about 30 mM, ammonium ion. Molar values are given because the weight depends on the particular ammonium salt chosen. For ammonium chloride the corresponding concentrations would be about 0.8 to about 2.4 g/L, preferably about 1.6 g/L. The nutrient medium used in the fermentations carried out under conditions of nitrogen excess and reported in Tables 2, 3 and 4 was the semisynthetic medium of Table 7 containing 5 g/L yeast extract (Difco) and 1.6 g/L NH$_4$Cl.

The amount of limiting nutrient, namely nitrogen, potassium or phosphorus, expressed as the concentration in the growth medium being fed to the fermenter, required to achieve a condition of growth limitation can be determined from Equations (1) and (2) and a knowledge of values for the growth yield with respect to the particular limiting nutrient and the maximum specific rate of substrate utilization ($q_s^{max}$). While these values may be strain specific, they can be experimentally determined and examples are given below.

The equations used to calculate the amount of limiting nutrient required to achieve a condition of nutrient deficiency or limitation are:

$$N^* = X^*/Y_n \quad (1)$$

where
  $N^*$ = the amount of source of nutrient, g;
  $X^*$ = the dry mass of cells (dry wt biomass), g; and
  $Y_n$ = growth yield coefficient for a specified limiting nutrient, n; g dry biomass/g-atom nutrient source (see Table 9).

The value for $X^*$ in Equation (1) is determined by Equation (2):

$$X^* = S_r(D)/q_s^{max} \quad (2)$$

where
  $S_r$ = the concentration of substrate in the feed stream to the fermenter, g/L;
  $D$ = the dilution rate, hr$^{-1}$; and
  $q_s^{max}$ = the maximum observed specific rate of substrate uptake for the strain of Zymomonas being used in the continuous fermentation, g glu/g biomass-hr$^{-1}$; (see Table 10).

Experimentally determined values of various growth yield coefficients ($Y_n$) for Z. mobilis strain ATCC 29191 with respect to different sole sources of assimilable nitrogen are given in Table 8.

TABLE 8

Observed Values of Growth Yields
(Z. mobilis ATCC 29191)

| Nitrogen Source | Growth Yield $Y_n$ |
|---|---|
| Yeast Extract (Difco) | 0.45 g dry biomass/g YE |
| Ammonium Chloride | 1.87 g dry biomass/g NH$_4$Cl |
| Ammonium Sulphate | 1.52 g dry biomass/g (NH$_4$)$_2$SO$_4$ |

Growth yield coefficients ($Y_n$) with respect to nitrogen, phosphorus and potassium were calculated from steady state biomass concentrations in respectively limited chemostat cultures at a fixed dilution rate of 0.15 hr$^{-1}$, a constant temperature of 30° C. and a pH of 5.5. In each case the entering glucose concentration was approximately 100 g/L. The results are summarized in Table 9. The value of growth yield with respect to potassium is influenced by the [Na$^+$] such that $Y_K$ decreases with increasing concentration of Na$^+$ in the culture medium. The titrant used to maintain pH was NaOH. Observed values for different growth yields for Z. mobilis are in good agreement with general values cited in the literature with respect to the elemental composition (% w/w) of bacteria.

TABLE 9

Calculated Values of Growth Yields
(Z. mobilis ATCC 29191)

| Type of Limiting Nutrient, n | $Y_n$ Growth Yield (g biomass/g atom) | Composition of Biomass % w/w |
|---|---|---|
| Nitrogen (N) | 7.1 | 14 |
| Phosphorus (P$_i$) | 44 | 2.3 |
| Potassium (K$^+$) | 33 | 3.0 |

The values given in Table 9 can be substituted in Equation (1). It will be understood that these values may vary with the fermentation system and operating techniques and should be confirmed by experimentation in the system under study or in question.

It has been suggested in the literature that the values for $q_s^{max}$ and $q_p^{max}$ are stain specific traits in Z. mobilis. In any event, $q_s^{max}$ and $q_p^{max}$ for the strain of interest can best be determined by means of non-carbon limitation under steady-state conditions in continuous culture in a chemostat. The value for $q_s^{max}$ may vary depending on the nature of the limiting nutrient and the particular strain of Z. mobilis chosen, but $q_s^{max}$ is generally about 7 to about 10 g glucose/g cell-hr$^{-1}$. Experimentally determined values of $q_s^{max}$ for nutrient-limited fermentations by the strain ATCC 29191 are given in Table 10.

TABLE 10

Observed Average Values of Maximum Specific Rate of Glucose Uptake for Nutrient-Limited Fermentation by Strain ATCC 29191 in Continuous Culture in a Chemostat

| Type of Limiting Nutrient, n | Chemical Identity of Limiting Nutrient | $q_s^{max}$ (g glucose/ biomass-hr$^{-1}$) | $Y_{X/n}$ (g glu/g of n) |
|---|---|---|---|
| Nitrogen | NH$_4$Cl | 8.3 | 1.87 |
| | (NH$_4$)$_2$SO$_4$ | 8.3 | 1.52 |
| | Yeast Extract (Difco) | 8.3 | 0.45 |

TABLE 10-continued

Observed Average Values of Maximum Specific Rate of Glucose Uptake for Nutrient-Limited Fermentation by Strain ATCC 29191 in Continuous Culture in a Chemostat

| Type of Limiting Nutrient, n | Chemical Identity of Limiting Nutrient | $q_s^{max}$ (g glucose/ biomass-hr$^{-1}$) | $Y_{X/n}$ (g glu/g of n) |
|---|---|---|---|
| Potassium | KCl | 7.5 | 17 |
| Phosphate | KH$_2$PO$_4$ | 7.2 | 10 |

The values in Table 10 can be substituted in Equation (2), once again subject to confirmation in the system under study.

The observed $q_s^{max}$ for potassium-limited *Z. mobilis* strain ATCC 29191 has been found to be 7.5 g glucose/g biomass-hr$^{-1}$, and the value for the growth yield ($Y_K$) with respect to KCl has been found to be 17 g biomass/g KCl. The observed value for $Y_K$ is 33 g biomass/g K$^+$, which is equivalent to saying that the biomass is 3% w/w potassium. Equations (1) and (2) can also be used to predict the amount of potassium (e.g. as KCl) required to achieve a condition of potassium limitation in continuous culture at various values for the concentration of glucose in the feed stream ($S_r$) and dilution rate (D).

The observed average value for $q_s^{max}$ for a phosphorus-limited culture of *Z. mobilis* is 7.2 g glu/g biomass-hr$^{-1}$ and the growth yield with respect to phosphorus (as potassium dihydrogen phosphate) is 10 g biomass/g KH$_2$PO$_4$. The observed $Y_P$ is 44 g biomass/g P, which is equivalent to biomass being 2.3% w/w with respect to its phosphorus content. These values can be substituted appropriately into Equations (1) and (2) in order to predict the amount of phosphorus required to achieve a condition of phosphorus-limitation at various values of $S_r$ and dilution rate.

The values in Tables 8 and 9 were determined at various values for $S_r$ and D. As mentioned previously, because *Z. mobilis* is sensitive to ethanol at concentrations in excess of about 5% (w/v), there is an upper limit to the practical value of $S_r$, namely about 150 g fermentable sugar/L.

The following Examples illustrate working embodiments of this invention.

EXAMPLE 1

Continuous ethanol fermentations were performed in apparatus similar to that described in the FIGURE. Bench-top chemostats (Model C30, New Brunswick Scientific Co., N.J.) were used in which the constant working volume (V) of 350 ml was established and maintained by means of an attached overflow tube. The culture was agitated by means of a pair of turbine six-blade impellers operating at 200 RPM. The temperature was controlled at 30° C. and the pH was monitored using a combination Ingold electrode coupled to a Model pH-40 (New Brunswick Scientific) pH analyzer. The addition of titrant (KOH) was controlled automatically by the pH controller and maintained at 5.5. The vessel was not sparged with gas of any kind except during start-up when oxygen-free N$_2$ was used at a rate of approximately 0.5 v/v/m.

The chemical composition of the semi-synthetic culture medium is described in Table 7. The concentration of glucose was 20, 60 or 110 g/L. Yeast extract obtained from Difco was the sole source of assimilable nitrogen added to the culture medium (i.e., ammonium chloride was not added). In order to achieve a condition of nitrogen-excess growth, 5 g/L yeast extract were added to the basal salts medium (at all concentrations of glucose). For nitrogen-limitation the amount of yeast extract added to the salts medium depended on the amount of glucose in the medium such that for media containing 20, 60 and 110 g glucose/L, yeast extract in amounts of 0.8, 2.4 and 4.4 g, respectively, were added per liter (L).

Polypropylene glycol 2025 was added to the medium as an antifoaming agent at a concentration of 0.1 ml/L. Media were prepared and autoclaved in 13 L pyrex carbuoys. Sterile culture medium was fed to the fermenter at a constant rate (F) by means of a peristaltic pump such that the dilution rate (calculated as F/V) was 0.15/hr$^{-1}$. The fermenter was inoculated (15% v/v) with *Z. mobilis* ATCC 29191, which had been grown overnight in medium of similar composition in a non-agitated flask incubated at 30° C. Flow to the fermenter was not commenced until the culture was in late-exponential phase of growth. Growth and biomass concentration were determined as dry weight of culture collected on preweighed microporous filters (Millipore Corp., 0.45 μm pore size). Sampling the biomass and weighing the dry cells has been found to be much more accurate and reliable than turbidity measurement or measurements made by indirect methods. Steady-state was presumed to have occurred after a minimum of 4 culture turnovers, a turnover being equivalent in time to the reciprocal of the dilution rate. Glucose was determined using a YSI Glucose Analyzer (Model 27, Yellow Springs Instrument Co., Ohio). Ethanol was measured by HPLC (HPX-87H Aminex, 300×7.8 mm column, from Bio-Rad, Burlington, Ont. Can.). The culture was routinely examined for contamination both by microscopic assessment and by plating on selective diagnostic agar media.

The specific rate of glucose uptake, $q_s$, (g glucose consumed/g biomass-hr$^{-1}$), was calculated as follows:

$$q_s = \frac{[S_r - S_o]D}{X}$$

where $S_r$ and $S_o$ represent the concentration of fermentable sugar in the feed reservoir and fermenter effluent, respectively;

D = the dilution rate (hr$^{-1}$); and

X = the dry weight culture biomass concentration (g/L).

Similarly, the specific rate of ethanol formation, $q_p$, (g ethanol/g biomass-hr$^{-1}$) was calculated as follows:

$$q_p = \frac{[P]D}{X}$$

where [P] represents the steady state ethanol concentration.

The results of this experiment are summarized in Table 2.

EXAMPLE 2

The same procedure was followed as in Example 1 except the sole source of nitrogen was ammonium chloride (no yeast extract was added to the medium and as such it is referred to as a defined salts medium). Table 2 shows the amount of ammonium chloride (NH$_4$Cl) used at different values for $S_r$ with respect to glucose, these being 0.19, 0.59 and 1.10 g NH$_4$Cl/L for $S_r$ glucose values of 20, 60 and 110 g/L, respectively.

EXAMPLE 3

The same procedure was followed as in EXAMPLE 1 except that the sole source of assimilable nitrogen was ammonium sulfate (AS). The amounts added and the results obtained are shown in Table 2.

EXAMPLE 4

Experiments were performed with *Z. mobilis* strain ATCC 31821. The results were substantially the same as those observed with strain ATCC 29191.

EXAMPLE 5

Experiments were performed with *Z. mobilis* strain ATCC 10988. The results were substantially the same as those observed with strain ATCC 29191.

EXAMPLE 6

Experiments were performed to show the amount of assimilable nitrogen required to achieve nitrogen-limitation as a function of dilution rate. The results are summarized in Table 3. $S_f$ was constant at 110 g/L and the dilution rate was set at 0.1, 0.15 and 0.2 $hr^{-1}$. The sole sources of nitrogen were yeast extract (Difco), ammonium chloride and ammonium sulphate. Although the results shown in Table 3 were obtained with strain ATCC 29191, substantially similar results were observed with both ATCC 31821 and ATCC 10988.

EXAMPLE 7

Table 4 summarizes the results of an experiment with ATCC 29191 to illustrate the effect of end-product (ethanol) inhibition on the general formula for predicting fermentation performance under conditions of nitrogen excess and nitrogen limitation. Even when the continuous fermenter was operated near its upper limit with respect to ethanol concentration, the specific activities ($q_s$ and $q_p$) of the culture were improved by imposing the condition of nitrogen limitation.

EXAMPLE 8

Experiments were performed to show the amount of potassium required to achieve potassium-limitation as a function of glucose concentration at a constant dilution rate for ATCC 29191. D was constant at 0.15 $hr^{-1}$, the pH was controlled with NaOH at 5.5 and $S_f$ was set at 20, 60 and 110 g/L. The sole source of potassium was KCl. The concentration of KCl and results obtained are summarized in Table 5.

EXAMPLE 9

Experiments were performed to show the amount of assimilable phosphorus, as $KH_2PO_4$, required at various sugar concentrations to achieve maximal rate of sugar utilization and ethanol production by *Z. mobilis* strain ATCC 29191, in continuous culture in a chemostat at a fixed dilution rate of 0.15 $hr^{-1}$. A pH of 5.5 was maintained with KOH. The concentrations of $KH_2PO_4$ and the results obtained are shown in Table 4.

EFFECT OF TEMPERATURE ON NUTRIENT-LIMITED FERMENTATION

Microbial growth and product formation are the result of a complex series of biochemical reactions that are temperature dependent. Zymomonas strains have a broad range of temperatures within which metabolic processes will occur and an optimum temperature range within which the rate of product formation is maximized. As the temperature is increased toward the optimum temperature, the rate of product formation increases. Above the optimum temperature, the rate of product formation rapidly declines, due in part to an increasing cell death rate and reduced cell growth rate. Lower biomass level translates to incomplete fermentation in a continuous system unless the dilution rate is adjusted appropriately downwardly. This is because, at relatively high substrate concentrations in the fermenter feed, the specific rate of substrate uptake will increase with increasing temperature, but the reduced biomass decreases the capacity of the fermenter to process the same substrate load. Heretofore, the optimum temperature was not exceeded when the object was to obtain maximum conversion of substrate to product in the least possible time.

The effect of temperature on the maximum specific growth rate ($u_{max}$) of *Z. mobilis* strain ATCC 29191 in batch culture has been reported in the literature and is shown in Table 11. The culture medium contained 2% (w/v) glucose.

TABLE 11

The Effect of Temperature on the Maximum Specific Growth Rate of *Z. mobilis* ATCC 29191 in Batch Culture (2% glu and pH 5.5)

| Temperature (°C.) | $u_{max}$ ($hr^{-1}$) |
| --- | --- |
| 30 | 0.27 |
| 33 | 0.38 |
| 36 | 0.26 |

The data in Table 11 show that as the temperature in the culture medium was increased from 30° C. to 33° C., the maximum specific growth rate increased, but with a further increase in temperature from 33° C. to 36° C., the maximum specific growth rate declined. Thus, the optimum fermentation temperature for this system was about 33° C. Cell growth was inhibited above this temperature.

While increasing temperature affects cell growth as shown in Table 11, it has now been found that increasing temperature also affects substrate conversion and product formation. Table 12 shows the effect of increasing temperature on performance of a carbon-limited continuous fermentation by *Z. mobilis* strain ATCC 29191 in a chemostat at a constant dilution rate of 0.19 $hr^{-1}$. The substrate was fed to the chemostat as an aqueous solution containing 2% (w/v) glucose.

TABLE 12

Effect of Increasing Temperature on Performance of Carbon-limited Continuous Fermentation by *Z. mobilis* ATCC 29191 at Constant Dilution Rate (D = 0.19 $hr^{-1}$; 2% glu; pH 5.5)

|  | 30° C. | 33° C. | 36° C. |
| --- | --- | --- | --- |
| $S_f$(g/L) | 20.7 | 20.7 | 20.7 |
| $S_o$(g/L) | — | 0.1 | 0.5 |
| X (g/L) | 0.65 | 0.55 | 0.45 |
| $q_s$(g/g-$hr^{-1}$) | 5.9 | 7.25 | 8.8 |
| $q_p$(g/g-$hr^{-1}$) | 2.80 | 3.41 | 4.14 |
| $Y_{p/s}$(g/g) | 0.47 | 0.47 | 0.47 |

In the continuous fermentations reported in Table 12, the glucose concentration in the feed to the fermenter was maintained constant at 20.7 g/L. When the temperature in the fermentation medium was increased from 30° C. to 33° C., the biomass concentration (X) in the fermenter decreased, but this decrease was compensated for by an increase in the specific rate of glucose uptake ($q_s$). It will be observed, however, that glucose began to appear in the fermenter effluent (i.e. $S_o=0.1$ g/L) at 33° C.

When the temperature in the fermentation medium was further increased from 33° C. to 36° C., once again the biomass concentration in the fermenter declined, this time from 0.55 g/L to 0.45 g/L, but the decline was offset by a further increase in the specific rate of glucose uptake ($q_s$). The conversion of glucose to ethanol was incomplete and the concentration of glucose in the effluent ($S_o$) increased to 0.5 g/L. While the yield coefficient ($Y_{p/s}$) remained constant at 0.47 g/g, the presence of unconverted glucose in the effluent was unacceptable.

The effect of increasing temperature on the performance of K$^+$-limited continuous fermentation by Z. mobilis strain ATCC 29191 in a chemostat at a constant dilution rate of 0.15 hr$^{-1}$ is shown in Table 13. Potassium was supplied as KCl at a concentration of 0.13 g/L.

TABLE 13

Effect of Increasing Temperature on Performance of K$^+$-limited Continuous Fermentation by Z. mobilis ATCC 29191 at Constant Dilution Rate (D = 0.15 hr$^{-1}$)

|  | 30° C. | 35° C. |
|---|---|---|
| $S_r$ g/L | 110 | 110 |
| [KCl] g/L | 0.13 | 0.13 |
| X (g/L) | 2.2 | 1.48 |
| $q_s$ (g/g-hr$^{-1}$) | 7.5 | 8.9 |
| $Y_{KCl}$ (g/g) | 17 | 11.5 |
| $S_o$ (g/L) | — | 22 |

The data in Table 13 show that increasing the temperature in the fermentation medium from 30° C. to 35° C. at a constant glucose concentration in the feed stream of 110 g/L resulted in a decrease in the biomass concentration and an increase in the specific rate of glucose uptake ($q_s$). In this case, however, the yield coefficient ($Y_n$ where n=KCl) declined from 17 g/g KCl to 11.5 g/g KCl and the glucose concentration in the effluent increased from 0 g/L to 22 g/L. These changes in system performance would adversely affect process economics in a commercial operation.

Table 14 shows the effect of increasing temperature on performance of a K$^+$-limited continuous fermentation by strain ATCC 29191 in a chemostat at varying dilution rates. The substrate was fed to the fermenter as an aqueous solution containing 2% (w/v) glucose and at a fixed flow rate. Potassium was supplied as KCl at a concentration of 0.1 g/L.

TABLE 14

The Effect of Temperature on Kinetics of K$^+$-limited Z. mobilis Strain ATCC 29191

| Temp. (°C.) | $S_r$ (g/L) | $S_o$ (g/L) | D (hr$^{-1}$) | X (g/L) | $q_s$ (g/g-hr$^{-1}$) | $q_p$ (g/g-hr$^{-1}$) |
|---|---|---|---|---|---|---|
| 30.0 | 100 | 18.3 | 0.155 | 1.70 | 7.40 | 3.48 |
| 32.8 | 100 | 10.6 | 1.157 | 1.68 | 8.20 | 3.85 |
| 35.0 | 100 | 34.8 | 0.160 | 1.15 | 8.90 | 4.0 |

Increasing the temperature by 2°–3° C. resulted in more conversion of glucose to ethanol, i.e. from approximately 82% to 90%, as judged by the decrease in effluent glucose ($S_o$). However, further increase in temperature caused more glucose to appear in the effluent and the conversion fell to 65%. At 35° C. the morphology of the culture changed dramatically becoming very filamentous. The result of operation at 35° C. was a reduced cell density, and even though the $q_p$ was higher, the reduced biomass could not handle the sugar load.

The effect of increasing temperature on the performance of a K$^+$-limited continuous fermentation by Z. mobilis according to this invention is shown in Table 15. The fermentation was carried out by Z. mobilis strain ATCC 29191 in a chemostat at a constant dilution rate of 0.15 hr$^{-1}$. Potassium was supplied as KCl at concentrations indicated.

TABLE 15

Effect of Increasing Temperature on Performance of K$^+$-limited Continuous Fermentation by Z. mobilis Strain ATCC 29191 at Constant Dilution Rate (D = 0.15 hr$^{-1}$)

|  | 30° C. | 35° C. | 35° C. |
|---|---|---|---|
| $S_r$ g/L | 110 | 110 | 110 |
| [KCl] g/L | 0.13 | 0.13 | 0.16 |
| X (g/L) | 2.2 | 1.48 | 1.85 |
| $q_s$ (g/g-hr$^{-1}$) | 7.5 | 8.9 | 8.9 |
| $Y_{KCl}$ (g/g) | 17 | 11.5 | 11.5 |
| $S_o$ (g/L) | — | 22 | — |

The concentration of substrate to the fermenter was the same in all cases, i.e. 110 glucose/L. Comparing column 2 with column 3 in Table 15, when the fermentation temperature was increased from 30° C. to 35° C., the biomass concentration (X) decreased from 2.2 g/L to 1.48 g/L, while the specific rate of glucose uptake ($q_s$) increased from 7.5 to 8.9 g/g-hr$^{-1}$. The amount of glucose in the effluent ($S_o$) also increased from 0 to 22 g glucose/L, which was commercially unacceptable.

Comparing column 2 with column 4 in Table 15, it is seen that by increasing the concentration of the limiting nutrient according to this invention, i.e. [KCl] in this case, when the temperature was increased from 30° C. to 35° C., the biomass concentration (X) in the fermenter decreased from 2.2 g/L to 1.85 g/L while the specific rate of glucose uptake ($q_s$) increased from 7.5 to 8.9 g/g-hr$^{-1}$. However, there was substantially no glucose in the effluent from the fermenter when the concentration of the limiting nutrient was properly controlled, i.e. $S_o=0$.

These results demonstrate that this embodiment of the invention makes it possible to improve the performance of Zymomonas in continuous ethanol fermentation at increased temperatures. The specific rate of substrate uptake can be maintained, and even increased, at fermentation temperatures of about 33° to about 37° C. even though there is a lower biomass concentration in the fermenter. These results can be achieved without substantial amounts of substrate in the effluent from the fermenter. These results are made possible by carrying out continuous ethanol fermentation with Zymomonas strains under nutrient-limited conditions, where the limiting nutrient is nitrogen, potassium or phosphorus. The concentration of the limiting nutrient in the fermentation medium is increased with increasing temperature and decreased with decreasing temperature.

In summary, the processes of this invention make it possible to carry out a continuous fermentation by Z. mobilis at reduced biomass concentration in the fermenter, increased specific rate of substrate uptake, increased specific rate of product formation and substantially without substrate in the effluent by regulating the amount of limiting nutrient. The processes of this invention take into account the unexpected decrease in growth yield with respect to the limiting nutrient and adjust the amount of the nutrient in the medium accordingly. The fermentation system operates efficiently at a high temperature, such as 35° C., with respect to fermentation capacity, and at a higher specific rate of substrate uptake and a higher specific rate of product formation with a lower biomass concentration in the fermenter. As previously discussed, this can be of considerable advantage in designing and operating a continuous fermentation with cell recycle where the productivity is typically limited by the concentration of biomass that can be handled by the recycle device be it a filtration system, centrifuge or settler.

What is claimed is:

1. A continuous process for the production of ethanol, which comprises feeding an aqueous substrate solution substantially continuously to a fermentation medium containing a submerged culture of an organism of the genus Zymomonas;

cultivating said organism under anaerobic conditions at a temperature of about 33° C. to about 37° C. in an aqueous nutrient medium containing potassium and assimilable carbon, nitrogen and phosphorus until a recoverable quantity of ethanol is produced;

wherein said nutrient medium is limited in assimilable nitrogen such that the rate of growth of said organism is limited by the availability of assimilable nitrogen, and said nutrient medium contains said limiting nutrient in a concentration proportional to temperature of said fermentation medium, such that limiting nutrient concentration is increased as temperature increases and is decreased as said temperature decreases;

and wherein said process is conducted as a nutrient-limited fermentation and under conditions such that biomass expresses its maximal value for both $q_s$ and $q_p$ under conditions of nutrient limitation and said process is conducted at a lower concentration of substrate in effluent from the process than from a similar process conducted with a nutrient medium containing nitrogen in excess;

and wherein each of said processes is carried out at the same fermentation temperature, dilution rate and concentration of assimilable carbon.

2. Process according to claim 1 wherein fermentation is conducted at a temperature of about 27° C. to about 37° C.

3. Process according to claim 1 wherein fermentation is conducted in a fermentation medium having a pH of about 4.5 to about 6.5.

4. Process according to claim 1 wherein fermentation is conducted at a temperature of about 30° C. and a pH of about 5.5.

5. Process according to claim 4 wherein said organism is Z. mobilis strain ATCC 29191.

6. Process according to claim 5 wherein said substrate is comprised of glucose.

7. A continuous process for the production of ethanol, which comprises feeding an aqueous substrate solution substantially continuously to a fermentation medium containing a submerged culture of an organism of the genus Zymomonas;

cultivating said organism under anaerobic conditions at a temperature of about 33° C. to about 37° C. in an aqueous nutrient medium containing potassium and assimilable carbon, nitrogen and phosphorus until a recoverable quantity of ethanol is produced;

wherein said nutrient medium is limited in potassium, such that the rate of growth of said organism is limited by the availability of assimilable potassium, and said nutrient medium contains said limiting nutrient in a concentration proportional to temperature of said fermentation medium, such that limiting nutrient concentration is increased as temperature increases and is decreased as said temperature decreases;

and wherein said process is conducted as a nutrient-limited fermentation and under conditions such that biomass expresses its maximal value for both $q_s$ and $q_p$ under conditions of nutrient limitation and said process is conducted at a lower concentration of substrate in effluent from the process than from a similar process conducted with a nutrient medium containing potassium in excess;

and wherein each of said processes is carried out at the same fermentation temperature, dilution rate and concentration of assimilable carbon.

8. A continuous process for the production of ethanol, which comprises feeding an aqueous substrate solution substantially continuously to a fermentation medium containing a submerged culture of an organism of the genus Zymomonas;

cultivating said organism under anaerobic conditions at a temperature of about 33° C. to about 37° C. in an aqueous nutrient medium containing potassium and assimilable carbon, nitrogen and phosphorus until a recoverable quantity of ethanol is produced;

wherein said nutrient medium is limited in phosphorus such that the rate of growth of said organism is limited by the availability of assimilable phosphorus, and said nutrient medium contains said limiting nutrient in a concentration proportional to temperature of said fermentation medium, such that limiting nutrient concentration is increased as temperature increases and is decreased as said temperature decreases;

and wherein said process is conducted as a nutrient-limited fermentation and under conditions such that biomass expresses its maximal value for both $q_s$ and $q_p$ under conditions of nutrient limitation and said process is conducted at a lower concentration of substrate in effluent from the process than from a similar process conducted with a nutrient medium containing phosphorus in excess;

and wherein each of said processes is carried out at the same fermentation temperature, dilution rate and concentration of assimilable carbon.

9. Process according to claim 8 wherein fermentation is conducted in a fermentation medium having a pH of about 4.5 to about 6.5.

10. Process according to claim 7 wherein fermentation is conducted at a temperature of about 30° C. and a pH of about 5.5.

11. Process according to claim 10 wherein said organism is Z. mobilis strain ATCC 29191.

12. Process according to claim 11 wherein said substrate is comprised of glucose.

13. A continuous process for the production of ethanol, which comprises feeding an aqueous substrate solution substantially continuously to a fermentation medium containing a submerged culture of an organism of the genus Zymomonas;

cultivating said organism under anaerobic conditions at a temperature of about 33° C. to about 37° C. in an aqueous nutrient medium containing potassium and assimilable carbon, nitrogen and phosphorus until a recoverable quantity of ethanol is produced;

wherein said nutrient medium is limited in assimilable phosphorus and said nutrient medium contains said limiting nutrient in a concentration proportional to temperature of said fermentation medium, such that limiting nutrient concentration is increased as said temperature increases and is decreased as said temperature decreases;

and wherein said process is conducted as a nutrient-limited fermentation and under conditions such that biomass expresses its maximal value for both $q_s$ and $q_p$ under conditions of nutrient limitation and said process is conducted at a lower concentration of substrate in effluent from the process than from a similar process conducted with a nutrient medium containing phosphorus in excess; and wherein each of said processes is carried out at the same fermentation temperature, dilution rate and concentration of assimilable carbon.

14. Process according to claim 13 wherein fermentation is conducted at a temperature of about 27° C. to about 37° C.

15. Process according to claim 14 wherein fermentation is conducted in a fermentation medium having a pH of about 4.5 to about 6.5.

16. Process according to claim 13 wherein fermentation is conducted at a temperature of about 30° C. and a pH of about 5.5.

17. Process according to claim 16 wherein said organism is *Z. mobilis* strain ATCC 29191.

18. Process according to claim 17 wherein said substrate is comprised of glucose.

* * * * *